US00PP26559P3

(12) United States Plant Patent
Danziger

(10) Patent No.: US PP26,559 P3
(45) Date of Patent: Mar. 29, 2016

(54) ***PETUNIA* PLANT NAMED 'DRAY305'**

(50) Latin Name: *Petunia sensu wijsman*
Varietal Denomination: DRAY305

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 119 days.

(21) Appl. No.: 14/120,183

(22) Filed: May 2, 2014

(65) Prior Publication Data

US 2015/0319905 P1 Nov. 5, 2015

(51) Int. Cl.
*A01H 5/02* (2006.01)

(52) U.S. Cl.
USPC ..... Plt./356.23

(58) Field of Classification Search
USPC ..... Plt./356.1, 356.23
See application file for complete search history.

*Primary Examiner* — Susan McCormick Ewoldt
(74) *Attorney, Agent, or Firm* — Cassandra Bright

(57) ABSTRACT

A new and distinct *Petunia* cultivar named 'DRAY305' is disclosed, characterized by abundant flowering, mounded ball-shaped form, red flower color and extra large flower size. The new variety is a *Petunia*, normally produced as an outdoor garden or container plant.

2 Drawing Sheets

Figure 1:
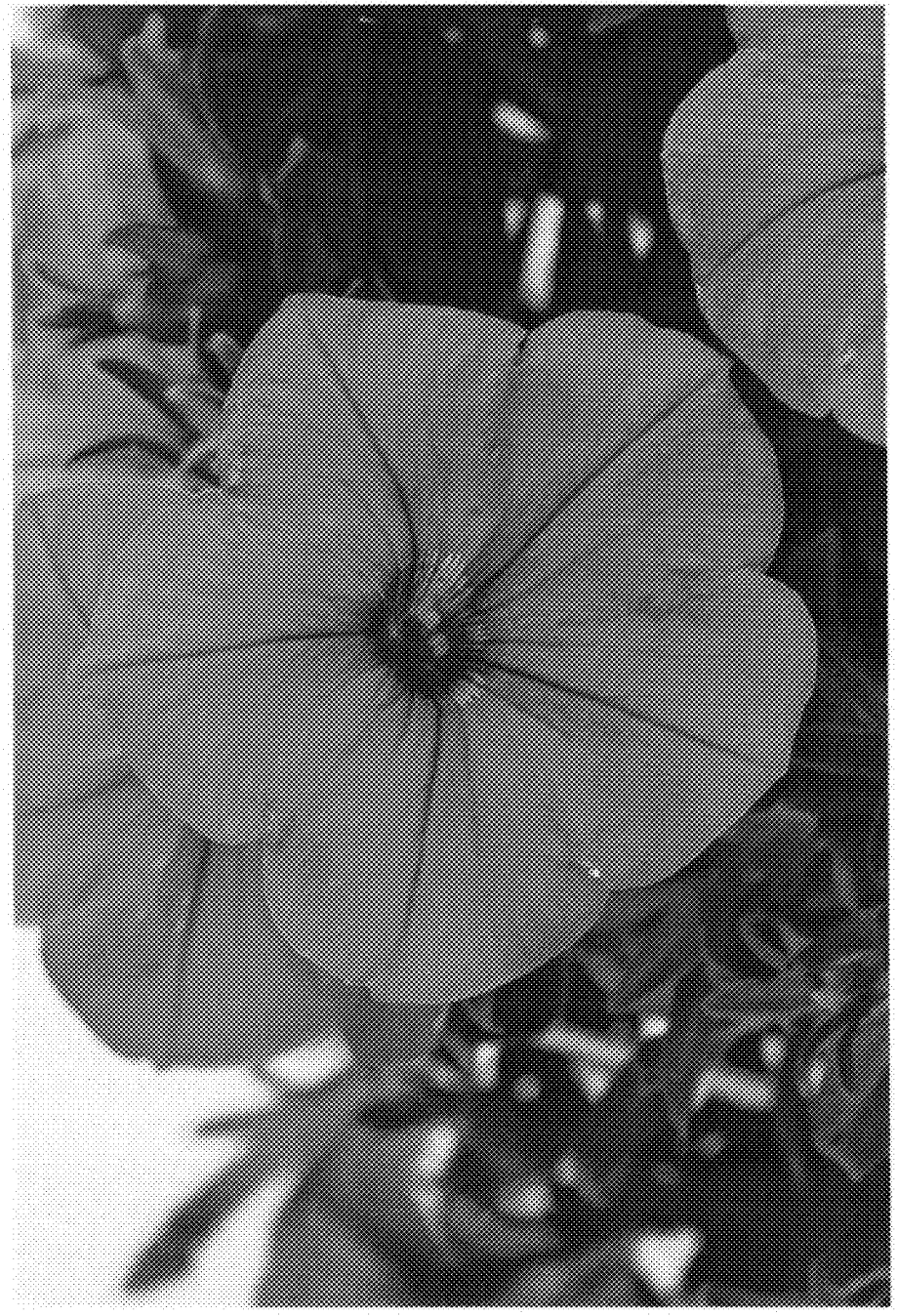

Latin name of the genus and species: *Petunia sensu wijsman.*

Variety denomination: 'DRAY305'.

BACKGROUND OF THE INVENTION

The new *Petunia* cultivar is a product of a planned breeding program conducted by the inventor, Gavriel Danziger, in Moshav Mishmar Hashiva, Israel. The objective of the breeding program was to produce new *Petunia* varieties for ornamental commercial applications. The cross resulting in this new variety was made during February of 2011.

The seed parent is the unpatented, proprietary variety referred to as *Petunia sensu wijsman*. 'cv. 10-4265'. The pollen parent is the unpatented, proprietary variety referred to as *Petunia sensu wijsman* 'cv. 10-4253'. The new variety was discovered in November of 2011 by the inventor in a group of seedlings resulting from the 2011 crossing, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in December of 2011 and has shown that the unique features of this cultivar are stable and reproduced true to type in more than 25 successive generations.

SUMMARY OF THE INVENTION

The cultivar 'DRAY305' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DRAY305' These characteristics in combination distinguish 'DRAY305' as a new and distinct *Petunia* cultivar:

1. Mounded, ball-shaped plant.
2. Very well branched with medium vigor.

3. Flower color is red.
4. Flower size is extra large.
5. Abundant flowering.

Plants of the new cultivar 'DRAY305' are similar to plants of the seed parent, *Petunia sensu wijsman* 'cv. 10-4265' in most horticultural characteristics, however, plants of the new cultivar 'DRAY305' differs in the following:

1. Mounded, ball shaped growth habit compared to the semi upright growth habit of the seed parent.
2. Larger plant size.
3. Different flower color, red compared to dark red color of the seed parent.
4. Larger flower size.
5. More abundant flowering.

Plants of the new cultivar 'DRAY305' are similar to plants of the pollen parent; *Petunia sensu wijsman* 'cv. 10-4253' in most horticultural characteristics, however, plants of the new cultivar 'DRAY305' differ in the following;

1. Mounded, ball shaped growth habit compared to the semi upright growth habit of the pollen parent.
2. More abundant branching.
3. Different flower color, red compared to light pink flower color of pollen parent.
4. Larger flower size.
5. More abundant flowering.

COMMERCIAL COMPARISON

Plants of the new cultivar 'DRAY305' are comparable to the commercial variety *Petunia* 'DANRAY5' U.S. Plant Pat. No. 20,973. The two *Petunia* varieties are similar in most horticultural characteristics; however, the new variety 'DRAY305' differs in the following:

1. Flower color is lighter.
2. Shorter, lighter colored leaves.
3. Less vigor.
4. Shorter branches.

Plants of the new cultivar 'DRAY305' can also be compared to the commercial variety *Petunia* 'DANRAY3', unpatented. These varieties are similar in most horticultural characteristics; however 'DRAY305' differs in the following:

1. Larger flower size.
2. Red flowers. The comparator has light purple flowers with dark purple veins.
3. Shorter branches
4. Less vigor.

BRIEF DESCRIPTION OF THE PHOTOGRAPHS

The accompanying photograph in FIG. 1 illustrates a close up of the flowers.

Figure 2:
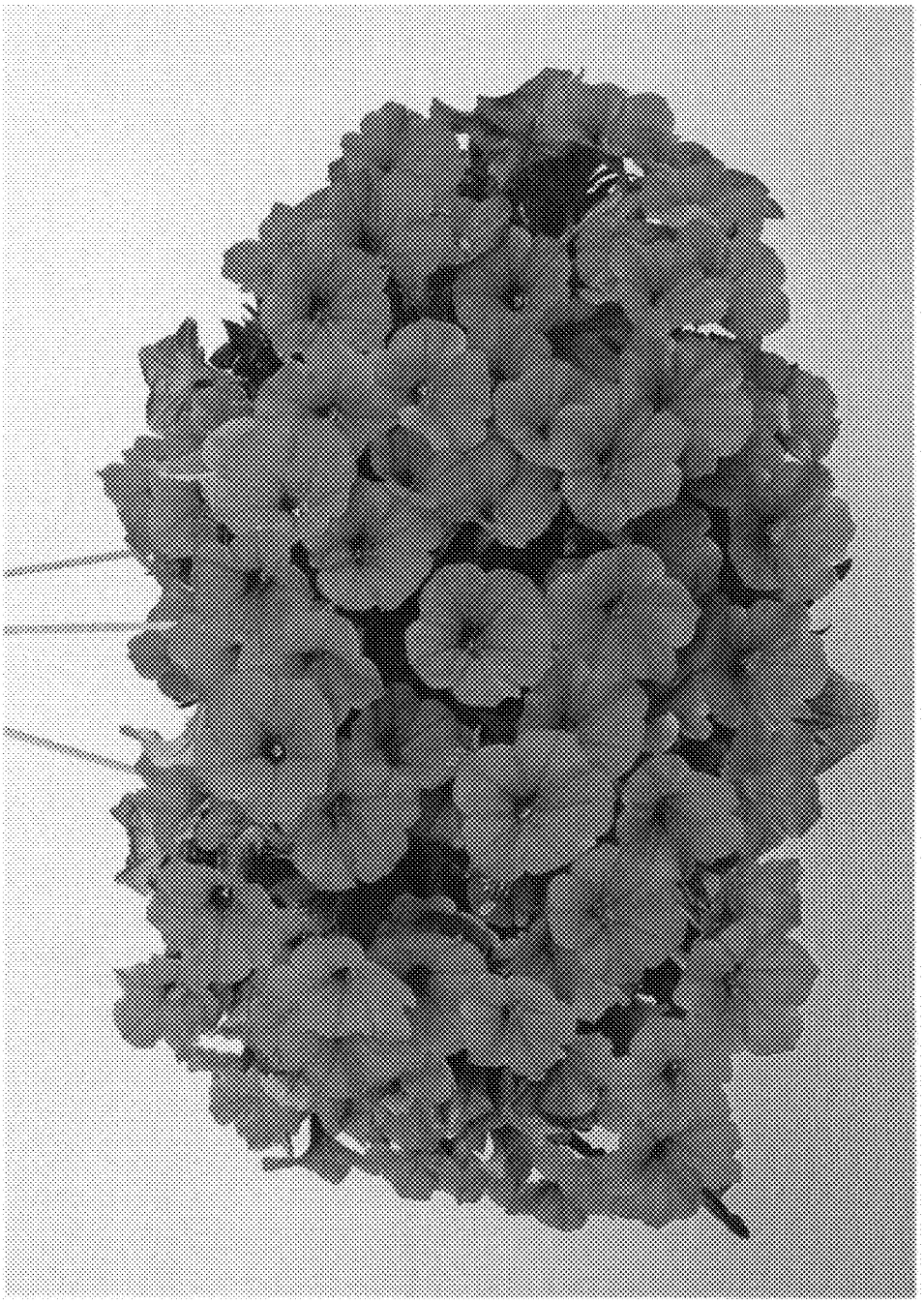

FIG. 2 illustrates in full color a typical plant of 'DRAY305' grown in a greenhouse, in a 13 cm pot. Age of the plant photographed is approximately 3 months from a rooted cutting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2007 except where general terms of ordinary dictionary significance are used. The following observations and measurements describe 'DRAY305' plants grown in a greenhouse, in Moshav Mishmar Hashiva, Israel. The growing temperature ranged from 20° C. to 35° C. during the day and from 17° C. to 23° C. during the night. General light conditions are bright, normal sunlight. Measurements and numerical values represent averages of typical plant types.

Botanical classification: *Petunia sensu wijsman* 'DRAY305'.

PROPAGATION

Time to initiate roots: About 10 to 14 days.
Root description: Fibrous.

PLANT

Age of plant described: Approximately 60 days from a rooted cutting.
Growth habit: Mounded.
Pot size of plant described: 13 cm.
Height: About 20 cm.
Plant spread: About 60 cm.
Growth rate: Medium.
Branching characteristics: Very well branched.
Length of primary lateral branches: About 20 cm.
Diameter of lateral branches: About 0.4 cm.
Quantity of primary lateral branches: 8.
Characteristics of primary lateral branches:
- *Form*.—Cylindrical.
- *Diameter*.—About 0.4 cm.
- *Color*.—RHS Yellow-Green 144.
- *Texture*.—Pubescent.
- *Strength*.—Good.

Internode length: About 2 cm.

FOLIAGE

Leaf:
- *Arrangement*.—Opposite.
- *Quantity*.—Approximately 25 per branch.
- *Average length*.—5.5 cm.
- *Average width*.—2.5 cm.
- *Shape of blade*.—Elliptic.
- *Apex*.—Acute.
- *Base*.—Acute.
- *Margin*.—Entire.
- *Texture of surfaces*.—Velvety.
- *Aspect*.—Mainly flat, attached at approximately 90 degrees.
- *Color*.—Young foliage upper side: RHS Green 137 C. Young foliage under side: RHS Green 137 C. Mature foliage upper side: RHS Green 137 B. Mature foliage under side: RHS Green 137 C.
- *Venation*.—Type: Pinnate. Venation color upper side: RHS Green 137 C. Venation color under side: RHS Green 137 D.
- *Petiole*.—Length: About 0.3 cm. Diameter: About 0.3 cm. Color: RHS Green 137 B.
- *Texture*.—Velvety.

FLOWER

Natural flowering season: Spring, Summer and Autumn.
Days to flowering from rooted cutting: About 30 days.
Inflorescence and flower type and habit: Axillary, single flower, salverform shape, outwardly facing.
Rate of flower opening: 2 to 3 days from bud to fully opened flower.
Flower longevity on plant: 3-6 days.
Approximate quantity of flowers per plant: About 60.
Persistent or self-cleaning: Self-cleaning.
Bud:
- *Shape*.—Tubular.
- *Length*.—About 5.5 cm.
- *Diameter*.—About 1 cm.
- *Color*.—RHS Greyed-Purple 185 A.

Flower size:
- *Diameter*.—About 7.5 cm.
- *Flower tube length*.—About 3.5 cm.
- *Flower tube diameter at distal end*.—1 cm.
- *Flower tube diameter at proximal end*.—0.4 cm.

Petals:
- *Length from throat*.—About 3.5 cm.
- *Width*.—About 3.5 cm.
- *Quantity*.—5.
- *Texture*.—Velvety.
- *Apex*.—Blunt.
- *Margin*.—Entire.

Color:
- *When opening*.—Upper surface: RHS Red 46 B. Lower surface: RHS Red 51 C.
- *Fully opened*.—Upper surface: RHS Red 46 C. Lower surface: RHS Red 51 C. Flower throat (inside): RHS Brown N 200 C. Flower throat, vein: RHS Black 202 A. Flower tube (outside): RHS Greyed-Purple 185 C. Flower tube, vein: RHS Green 137 C.
- *Fading*.—Petals fading to: RHS Red 47 B.

Calyx/sepals:
Quantity per flower.—5.
*Shape*.—Linear.
*Length*.—About 2.5 cm.
*Width*.—About 0.4 cm.
*Apex*.—Acute.
*Base*.—Fused.
*Margin*.—Entire.
*Texture*.—Velvety.
*Color*.—Upper Surface: RHS Green 137 B. Lower Surface: RHS Green 137 C.
Peduncle:
*Length*.—About 3 cm.
*Diameter*.—About 0.2 cm.
*Color*.—RHS Green 137 C.
*Orientation*.—45 degrees.
Fragrance: None.

REPRODUCTIVE ORGANS

Stamens:
*Number*.—5.
*Filament length*.—About 2.0 cm.
Anthers:
*Length*.—About 0.1 cm
*Shape*.—Rounded. .
*Color*.—RHS Yellow 8 C.
*Pollen*.—Color: RHS Yellow 8 C. Quantity: Plenty.
Pistil:
*Number*.—1.
*Length*.—About 3 cm.
*Style*.—Length: About 2.4 cm. Color: RHS Yellow-Green 144 D.
*Stigma*.—Shape: Rounded. Color: RHS Yellow-Green 144 A. Ovary Color: RHS Yellow-Green 144 B.

OTHER CHARACTERISTICS

Seeds and fruits: About 70 brown, rounded seeds of about 0.5 mm diameter, per one brown, conical capsule. Seeds minute, not effectively measured with an R.H.S. chart.
Disease/pest resistance: Neither resistance nor susceptibility to normal diseases and pests of *Petunia* has been observed.
Temperature tolerance: Tolerates a range from approximately 5° to 40° C.

What is claimed is:

1. A new and distinct cultivar of *Petunia* plant named 'DRAY305' as herein illustrated and described.

* * * * *